United States Patent
Auguste et al.

(10) Patent No.: US 7,268,177 B2
(45) Date of Patent: *Sep. 11, 2007

(54) THERMOPLASTIC ELASTOMER-BASED SOLID EMULSIONS

(75) Inventors: Stephane Auguste, Varois et Chaignot (FR); Nadege Desmaison, Dijon (FR)

(73) Assignee: Laboratoires Urgo, Chenove (FR)

( * ) Notice: Subject to any disclaimer, the term of this patent is extended or adjusted under 35 U.S.C. 154(b) by 289 days.

This patent is subject to a terminal disclaimer.

(21) Appl. No.: 10/514,251

(22) PCT Filed: Apr. 16, 2003

(86) PCT No.: PCT/FR03/01216

§ 371 (c)(1),
(2), (4) Date: Nov. 15, 2004

(87) PCT Pub. No.: WO03/087220

PCT Pub. Date: Oct. 23, 2003

(65) Prior Publication Data

US 2005/0176871 A1  Aug. 11, 2005

(30) Foreign Application Priority Data

Apr. 17, 2002 (FR) .................... 02 04780

(51) Int. Cl.
C08F 290/04 (2006.01)
C08F 51/00 (2006.01)

(52) U.S. Cl. ............... 524/504; 524/505; 524/517; 523/105; 523/111

(58) Field of Classification Search ........... 524/504, 524/505, 517; 523/105, 111
See application file for complete search history.

(56) References Cited

U.S. PATENT DOCUMENTS

| | | | |
|---|---|---|---|
| 4,369,284 A | 1/1983 | Chen | |
| H1022 H | 2/1992 | Holden et al. | 524/474 |
| 5,122,569 A | 6/1992 | Scheibelhoffer et al. | |
| 5,167,649 A | 12/1992 | Zook | |
| 5,552,495 A | 9/1996 | Miller et al. | |
| 6,576,712 B2 | 6/2003 | Feldstein et al. | |
| 2004/0148003 A1 | 7/2004 | Udipi et al. | |

FOREIGN PATENT DOCUMENTS

| | | |
|---|---|---|
| CA | 2 426 251 A1 | 4/2002 |
| EP | 0 723 571 | 12/1998 |
| EP | 0 758 009 | 3/1999 |
| EP | 0 991 730 | 2/2003 |
| FR | 2 815 636 | 4/2002 |
| JP | 54-143517 | * 11/1979 |
| JP | 07-059808 | * 3/1995 |
| WO | WO 02/22735 | 3/2002 |

OTHER PUBLICATIONS

Liu et al. "Preparation and Spectroscopic Properties of Phenanthrene-Labeled SEBS Triblock Copolymers". *Macromolecules*, vol. 32, No. 12, pp. 3957-3963 (Apr. 27, 1999).

Al-Sabagh et al. "Water-based non-ionic polymeric surfactants as oil spill dispersants". *Journal of Chemical Technology and Biotechnology*, vol. 74, pp. 1075-1081 (May 22, 1999).

Qunitana et al. "Crystallization and thermal behavior of poly (vinylidene fluoride)/.Poly [styrene-b- (ethylene-co-butylene)-b-styrene] blends functionalized with succinic groups". *Journal of Polymer Science: Part B: Polymer Physics*, vol. 32, pp. 201-204 (Mar. 11, 1993).

Lin et al. "Synthesis, characterization, and interfacial behaviors of poly(oxyethylene)-grafted SEBS copolymers". *Industrial & Engineering Chemistry Research*, vol. 39, No. 1, pp. 65-71 (Nov. 30, 1999).

Derwent Abstract, week 199347ndon: Derwent Publications Ltd., AN 1993-374751, Class A18, JP 05-279623 A, (Nippon Steel Chem Co), abstract.

Donatas Satas (Ed.) *Handbook of Pressure Sensitive Adhesive Technology, Second Edition*, Chapter 13, pp. 317 to 359 (1989).

* cited by examiner

*Primary Examiner*—Helen L Pezzuto
(74) *Attorney, Agent, or Firm*—Merchant & Gould P.C.

(57) ABSTRACT

The present invention relates to novel solid emulsions, characterised in that they comprise a thermoplastic elastomer of poly(styrene-olefin-styrene) block copolymer type, an aqueous phase, an oily phase and an amphiphilic copolymer.

Figure 1:
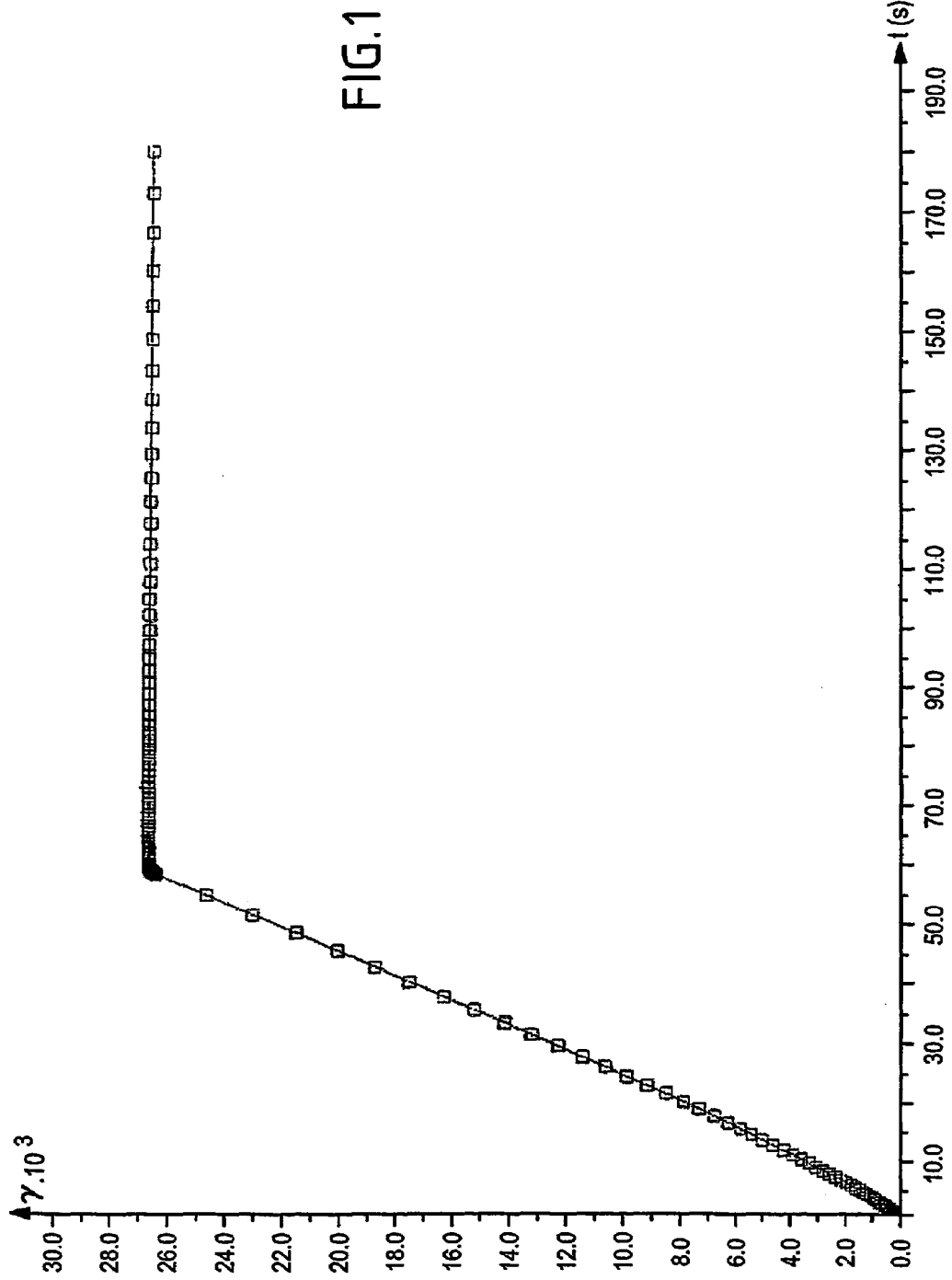

The invention also relates to the use of these novel solid emulsions notably for the preparation of products for medical, dermatological or cosmetological purposes which come into contact with a wound, skin or mucous membranes.

17 Claims, 2 Drawing Sheets

THERMOPLASTIC ELASTOMER-BASED SOLID EMULSIONS

The present invention relates to solid emulsions which comprise a thermoplastic elastomer of poly(styrene-olefin-styrene) copolymer type, an oily phase, an aqueous phase and an amphiphilic copolymer, as well as to their uses, particularly for medical, cosmetic or dermatological purposes.

Very many water-in-oil or oil-in-water type emulsions exist which have been developed in various applications such as the formulation of explosives, of fertilisers and, more particularly, for the preparation of products intended to be in contact with the skin, a wound, the mucous membranes or the semi-mucous membranes, which can be used for medical, cosmetic, dermatological or pharmaceutical purposes.

All these classical emulsions behave as products which are more or less viscous or pasty which, due to their lack of cohesion and elasticity, can be applied only by stretching, and once applied on the skin, tend to stick to it, even to soil clothes.

In order to remedy these problems and to give a physical consistency to these emulsions, it has been proposed to incorporate therein, in the aqueous or oily phase, consistence factors such as waxes or gellifiers.

However, the addition of these products does not solve the problems cited above entirely satisfactorily and renders the development of stable and well-tolerated emulsions more difficult. In fact, in order to stabilise the emulsions containing such consistance factors, it is necessary to incorporate therein significant amounts of one or more surfactant agents, with the correlative risk of increasing the problems of tolerance of these emulsions on the skin, a wound or the mucous membranes.

Finally, due to the fact that these emulsions are neither cohesive nor elastic once they are applied onto the skin, they cannot be removed reversibly in one piece.

Gel-type compositions are furthermore known which are prepared from a poly(styrene-olefin-styrene) block copolymer combined with a plasticizer, such as a plasticizing oil, such as a mineral oil in particular.

It is possible to obtain a wide range of gels which have good properties of elasticity and cohesion by adjusting the nature (grade, molar mass) and the proportion of these two elements.

These compositions, which can be used in very many fields, are, for example, described in U.S. Pat. No. 5,167,649 and U.S. Pat. No. 4,369,284.

However, these known compositions have the drawback of being totally hydrophobic due to the nature of their constituents. It is therefore impossible to incorporate water therein, and a gel of this type containing water therefore does not exist.

This hydrophobicity manifests itself by a certain number of major drawbacks in the case of their use on the skin, a wound or the mucous membranes. It is in fact impossible or very difficult to incorporate in these known compositions hydrophilic products, such as, for example, actives or adjuvants, the presence of which can prove to be indispensable.

Formulations containing such actives are difficult to prepare, and necessitate the addition of compounds which increase the cost of the manufacture of it, and the problems of tolerance with regard to the skin, a wound or the mucous membranes.

Moreover, the hydrophobicity of these known gels leads to the formation of an occlusive layer which, due to biological fluids (perspiration, exudation from the wound etc . . . ), causes phenomena of maceration, and correlative risks of tolerance.

Finally, these known gels, in contrast to the hydrogels which contain water, lack cosmetic approval and do not enable a sensation of cold or of freshness to be brought about upon contact of the skin, a wound or the mucous membranes.

It would therefore be desirable to have novel compositions at one's disposal which would combine the advantages of classical emulsions, and of gel type compositions based on poly(styrene-olefin-styrene) block copolymers, i.e. compositions which would contain both an aqueous phase and an oily phase and which would possess properties of cohesion and of elasticity enabling their manipulation, their shaping, their easy removal in one sole piece after application, and which in the case of their use on the skin, a wound or the mucous membranes, would be well-tolerated, stable, and susceptible of incorporating and of releasing hydrophilic or lipophilic products or actives, and, if necessary, of conferring a sensation of cold or of freshness.

An aim of the present invention is to solve the technical problem which consists in providing novel compositions which fulfill these objectives, which are in the form of emulsions, of water-in-oil or oil-in-water type, and which are elastic and cohesive, that will be designated in this Application under the term "solid emulsions".

Thus, according to a first aspect, the present Application covers a solid emulsion, characterised in that it comprises:
- a thermoplastic elastomer, which is selected from the block copolymers poly(styrene-olefin-styrene), poly(styrene-olefin), and their mixtures,
- an oily phase, which is constituted of a liquid plasticizer,
- an aqueous phase, and
- an amphiphilic ABA type block copolymer comprising two terminal thermoplastic poly(styrene) blocks A and one central elastomeric block B, in which the central block B is a poly(ethylene-butylene) sequence comprising grafted hydrophilic groups, it being possible for said ABA copolymer to be represented schematically by the following structure:

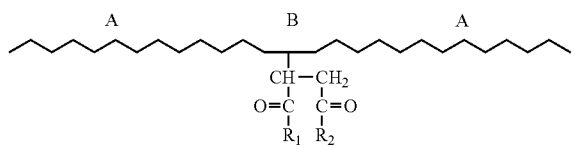

in which $R_1$ and $R_2$, which are identical or different, represent a hydrophilic group of average molar mass of less than 10,000, selected from the following groups:

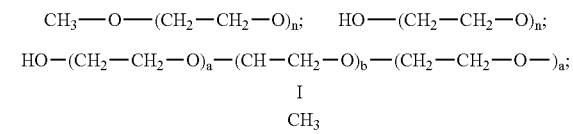

in which n, a and b represent an integer.

These solid emulsions possess an excellent shapability and their hardness can be easily regulated, and this enables products ranging from a cohesive gel to a solid to be obtained, which can be used not only in multiple fields of application, just as known block copolymer-based gels, but also in applications in which they can be placed in contact with the skin, a wound or the mucous membranes.

According to a second aspect, the present Application covers the use of these novel solid emulsions for the preparation of products which are intended for medical, dermatological or cosmetological purposes and which are susceptible to coming in contact with a wound, skin or mucous membranes.

The detailed description which follows of the various constituents of the solid emulsions according to the invention will enable better understanding the nature of the applications of this invention.

These amphiphilic copolymers are obtained by grafting hydrophilic compounds onto a particular SEBS copolymer.

This particular copolymer comprises succinic anhydride functions which are distributed along the elastomeric poly (ethylene-butylene) chain, which are obtained by reaction of maleic anhydride with the poly(ethylene-butylene) sequence, and which will be called "maleated SEBS" in the following.

This maleated SEBS copolymer, which serves as the basis for the preparation of the amphiphilic copolymers according to the invention, can be represented schematically by the following formula:

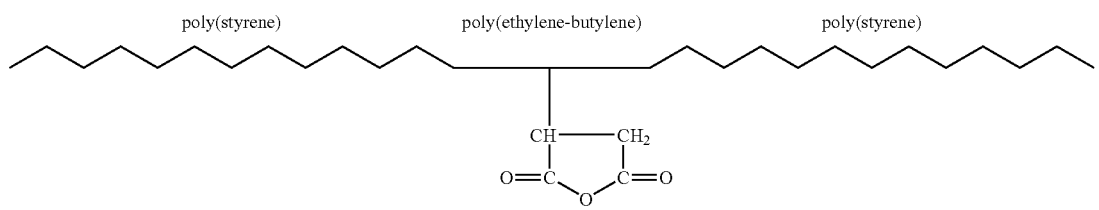

DESCRIPTION OF THE INVENTION

The amphiphilic copolymer which is used in the preparation of the solid emulsions according to the invention is an ABA type block copolymer comprising two terminal thermoplastic poly(styrene) blocks A and one central elastomeric block B, in which this central block B is a poly (ethylene-butylene) sequence comprising grafted hydrophilic groups, it being possible for said amphiphilic copolymer ABA to be represented schematically by the following structure:

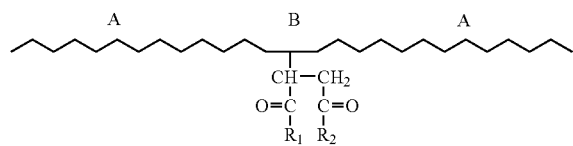

in which $R_1$ and $R_2$, which are identical or different, represent a hydrophilic group of average molar mass of less than 10,000, selected from the following groups:

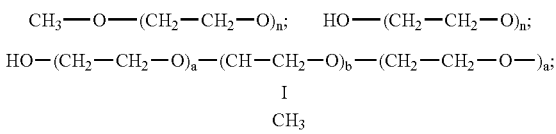

in which n, a and b represent an integer.

Advantageously, within the context of the present invention, the amphiphilic copolymers will be preferred in which $R_1$ and $R_2$ are identical.

Amongst these, the amphiphilic copolymers will preferably be used in which $R_1$ and $R_2$ represent a $CH_3$—O—$(CH_2$—$CH_2$—$O)_n$ group, particularly of average molar mass of between 1,000 and 8,000 and more particularly of average molar mass equal to 2,000 (i.e.=45).

For reasons of simplicity, only one sole succinic anhydride group has been represented in this formula on the poly(ethylene-butylene) sequence. It is obvious that this sequence in reality comprises several succinic anhydride groups. This simplification has also been used in order to schematically represent the amphiphilic copolymers used within the context of the present invention.

A maleated SEBS marketed by the company SHELL under the designation Kraton G 1901® will be preferred as maleated SEBS, which contains 2% by weight of succinic anhydride functions fixed onto the elastomeric chain and 28% by weight of polystyrene.

It is these anhydride functions which will serve to graft the hydrophilic compounds by chemical reaction between the hydrophilic compound and the anhydride or its acid form.

According to the conditions of storage, and particularly according to the degree of drying of this maleated SEBS, a part of these succinic anhydride functions can in fact be present as their acid forms after opening of the anhydride in the presence of water. The reaction then takes place as well between the acid functions and the hydrophilic compound.

The hydrophilic compounds which are grafted onto the maleated SEBS are of 3 types:

A/ Polyethyleneglycols, Hereinafter Referred to as the Abbreviation "PEGs"

These are hydrophilic, hygroscopic and heat-stable polymers. They are used in very many industrial fields. They are well-known to the person skilled in the art. They are short-chain polymers which possess hydroxyl functions on the extremities. Their average molar mass varies from 200 to 20,000.

Their composition corresponds to the following structure:

HO—$(CH_2$—$CH_2$—$O)_n$—H, in which n represents an integer.

Such products are for example marketed by the company Aldrich under the designation poly(ethylene glycol) followed by the average molar mass of the PEG considered, e.g. poly(ethyleneglycol) 2,000.

Within the context of the present invention, only amphiphilic copolymers in which the PEGs of average molar mass less than or equal to about 10,000 (n thus having at the maximum a value of 230) are used. Beyond, and the grafting reaction does in fact become difficult, even impossible.

Advantageously, the PEGs will be used which have an average molar mass of between 1,000 and 8,000, particularly the PEG which has an average molar mass of 2,000 (n=45).

B/ Polyethyleneglycol Mono Methyl Ethers Hereinafter Referred to as the Abbreviation "PEGMEs"

These are also short-chain polymers which are used like the PEGs in very many fields and which are well-known to the person skilled in the art.

They have the following structure:

$CH_3$—O—$(CH_2'CH_2$—O$)_n$—H, in which n is an integer, and their average molar mass ranges from 200 to 20,000.

Such products are for example marketed by the company Aldrich under the designation poly(ethyleneglycol)methyl ether followed by the average molar mass of the PEGME considered, e.g. poly(ethyleneglycol)methylether 2,000.

Within the context of the present invention, amphiphilic copolymers will be used in which, just as for the PEGs, only the PEGMEs of average molar mass less than or equal to about 10,000 (n having at the maximum a value of 230) are used.

Advantageously, the PEGMEs will be used which have an average molar mass of between 1,000 and 8,000, particularly the PEGME which has an average molar mass of 2,000 (n=45).

C/ Polyethylene-Polypropyleneglycol Copolymers

These are very well-known copolymers which will be designated hereinafter as the abbreviation PEO/PPO/PEO.

These are tri-block copolymers the central part of which is a polypropylene oxide block and the extremities of the polyethylene oxide blocks which have the following structure:

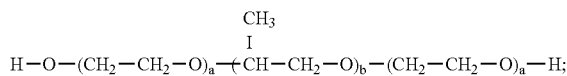

in which a and b are integers.

They are often designated as the general term "poloxamer".

Very many grades exist for these products which are characterised by the values a and b which define their average molar masses. The following can thus be cited:

poloxamer 124: a=12 b=20 average molar mass of between 2,090 and 2,360, poloxamer 188: a=80 b=27 average molar mass of between 7,680 and 9,510, poloxamer 407: a=101 b=56 average molar mass of between 9,840 and 14,600.

They are marketed for example by the company BASF under the designation Pluronic®.

Here, just as before, only the PEO/PPO/PEO of average molar mass less than or equal to about 10,000 will be used.

Within the context of the present invention, a PEO/PPO/PEO will be preferred of molar mass neighbouring 2,000, such as, for example, the product marketed under the designation poly(ethyleneglycol)-block-poly(propyleneglycol)-block-poly(ethyleneglycol) 1900, by the company Aldrich, of average molar mass equal to 1,900.

The amphiphilic copolymers which can be used within the context of the present invention can be prepared easily by a reaction of esterification between the succinic anhydride functions of the maleated SEBS and the hydroxyl functions of the PEG, PEGME or PEO/PPO/PEO used.

The reaction of an alcohol with an anhydride function gives, reversibly, an ester. Within the context of the present invention, this esterification can be represented by the following simplified scheme:

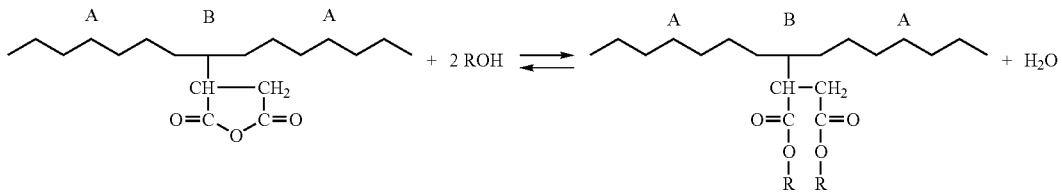

An excess of hydroxyl functions with respect to the anhydride functions is introduced, so as to promote the esterification reaction. Advantageously, the reaction is catalysed by an acid, and the water formed is removed by azeotropic distillation, in order to displace the equilibrium towards the grafted product. The reaction is preferably carried out under an inert atmosphere.

Thus, said amphiphilic copolymers are prepared according to a method in which a reaction of esterification is carried out between the succinic anhydride functions borne by the poly(ethylene-butylene) part of a poly(styrene)-poly(ethylene-butylene)-poly(styrene)copolymer (maleated SEBS) and the hydroxyl functions of a hydrophilic compound which is selected from polyethyleneglycols, (PEG), polyethyleneglycol mono methyl ethers (PEGME) and copolymers of polyethylene-propylene glycol (PEO/PPO/PEO) of average molar mass of less than or equal to 10,000, or their mixtures, preferably in the presence of an acid catalyst, by removing the water formed and with an excess of hydroxyl functions with respect to the succinic anhydride functions of the maleated SEBS.

More specifically, the synthetic method is the following:

The maleated SEBS is dissolved in the hot and with agitation, in a solvent, preferably toluene (at about 120° C., the reflux temperature of the solvent).

Apart, a solution is prepared of at least one hydrophilic compound (PEG, PEGME, PEO/PPO/PEO or their mixtures) by heating the latter compound(s) at its (their) melting temperature(s), with agitation, in a solvent, preferably toluene. Advantageously, an excess of hydrophilic compounds is used. The number of hydroxyl functions compared to the number of anhydride functions can vary from 2.5 to 20.

A catalytic amount (around a few drops) of acid, e.g. sulphuric acid, is added, and then the solution of hydrophilic compound(s) in the solvent prepared beforehand, to the solution of the maleated SEBS copolymer obtained beforehand, with agitation and keeping under reflux.

This mixture is agitated under azeotropic distillation, under reflux for 30 minutes to 5 hours according to the nature of the hydrophilic compound(s), until the complete reaction of esterification between the anhydride functions (or their eventual acid forms) of the succinic groups of the maleated SEBS and the hydroxyl functions of the hydrophilic compound(s). The extent of the reaction is tracked by using techniques which are well-known to the person skilled in the art, e.g. by infrared spectroscopy until the absorption peak of the carbonyls of the anhydride, i.e. 1,785 cm$^{-1}$, has disappeared.

The reaction mixture is then precipitated in the hot at about 90-100° C. in an adequate precipitation solvent, such as, for example, ethanol or an ethanol/water mixture, said precipitation solvent representing about 4 times the volume of the whole of the reaction solvents used.

After filtration, the residual solvents are removed from the amphiphilic SEBS copolymer obtained, by evaporation in the oven under vacuum at 40-50° C.

It is thus necessary to purify this latter product in order to remove the hydrophilic compound(s) PEG, PEGME or PEO/PPO/PEO used in excess, which is (are) still present.

The amphiphilic polymer obtained is therefore re-dissolved under agitation at about 90 to 110° C. in toluene, and the solution obtained is re-precipitated in the same solvent and the same volume as during the precipitation step carried out before at the end of the synthesis.

Similarly, the amphiphilic SEBS copolymer is recovered by filtration and is dried again in the oven under vacuum at 40-50° C.

This purification step is repeated until the total removal of the hydrophilic compound(s) by checking the absence of the peak of this (these) latter compound(s), in accordance with techniques which are well-known to the person skilled in the art, by gel permeation chromatography (GPC).

Within the context of the present invention, this amphiphilic copolymer will be used in the solid emulsions at a concentration of the order of 0.05% to 20% by weight with respect to the total weight of the composition.

According to a preferred embodiment of the invention, an amphiphilic ABA type block copolymer will be used comprising two terminal thermoplastic poly(styrene) blocks A and one central elastomeric block B, in which this central block B is a poly(ethylene-butylene) sequence comprising grafted hydrophilic groups, it being possible for said amphiphilic copolymer ABA to be represented by the following structure

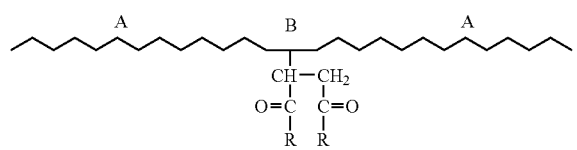

in which R represents a CH$_3$—O—(CH$_2$—CH$_2$—O)$_n$ group of average molar mass equal to 2000, i.e. n=45.

Such an amphiphilic copolymer will more particularly be preferred which has an average molar mass, measured by gel permeation chromatography, of the order of 50,000 daltons.

Preferably, this latter copolymer will then be used in the solid emulsions at a concentration of the order of 0.05 to 20%, particularly 0.05 to 5% by weight with respect to the total weight of the composition.

The thermoplastic elastomers of (styrene-olefin-styrene) block copolymer type or (styrene-olefin) block copolymer type which can be used within the context of the present invention are those which are usually used by the person skilled in the art in the preparation of compositions such as, for example, pressure-sensitive adhesives and reference in this respect may be made to the book edited in 1989 by Donatas Satas <<Handbook of Pressure Sensitive Technology>>, 2$^{nd}$ Edition, Chapter 13, pages 317 to 359, and to European Patent Applications published under the numbers EP 758 009 or EP 723 571, or to the prior art documents mentioned above.

These are therefore either ABA type triblock copolymers comprising two terminal thermoplastic styrene blocks A and one central elastomeric sequence B which is an olefin, or AB type diblock copolymers comprising a thermoplastic styrene block A and an elastomeric sequence B which is an olefin. The olefinic sequences B of these copolymers can be constituted of unsaturated olefins such as, for example, isoprene or butadiene, or of saturated olefins such as, for example, ethylene-butylene or ethylene-propylene.

It will be possible, within the context of the present invention, to use the whole of these two products alone or as a mixture.

In the case of a mixture of ABA triblock copolymers and of AB diblock copolymers, it will be possible to employ commercial mixtures of ABA triblock copolymers and AB diblock copolymers which are already available, or to make a mixture in any proportion selected beforehand from two independent products.

The products having unsaturated central sequence are well-known to the person skilled in the art and are for example marketed by the company SHELL under the designation KRATON®. The products marketed under the designations KRATON® D 1107 or KRATON® D 1161 can also be cited for the poly(styrene-isoprene-styrene) (abbreviated to SIS) copolymers and the product marketed under the designation KRATON® D 1102 can be cited for example for the poly(styrene-butadiene-styrene) copolymers. Other poly(styrene-isoprene-styrene) copolymers are also marketed by the company EXXON CHEMICAL under the designation VECTOR®, such as, for example, the product marketed under the designation VECTOR® 4113. The product marketed by the company EXXON CHEMICAL under the designation VECTOR® 4114, in which B is isoprene, can be cited as an example of a commercial mixture of ABA triblock and AB diblock copolymers.

All these copolymers based on isoprene or butadiene in general have a styrene content of between 10 and 52% by weight with respect to the total weight of said copolymer.

Within the context of the present invention, triblock poly(styrene-isoprene-styrene) block copolymers will be preferred having a styrene content of between 14 and 30% by weight with respect to the weight of said SIS, particularly the product marketed by the company SHELL under the designation KRATON® D 1161.

The products having a saturated central sequence are also well-known to the person skilled in the art and are for example marketed by the company SHELL under the designation KRATON® G for the poly(styrene-ethylene-butylene-styrene) (abbreviated to SEBS) block copolymers such as, for example, the products marketed under the designations KRATON® G 1651 or KRATON® G 1654, or by the company KURARAY under the designation SEPTON® for the poly(styrene-ethylene-propylene-styrene) (abbreviated to SEPS) block copolymers.

The product the olefinic sequence of which is ethylene-butylene marketed by the company SHELL under the designation KRATON® G 1657 can be cited as an example of commercial mixtures of triblock-diblock copolymers.

The mixture of a triblock SEBS can be cited as an example of a particular triblock-diblock mixture that can be used within the context of the present invention, such as the product marketed by the company SHELL under the designation KRATON® G 1651, with a poly(styrene-olefin) diblock material such as the poly(styrene-ethylene-propylene) marketed by the company SHELL under the designation KRATON® G 1702.

Within the context of the present invention, SEBS or SEPS triblock copolymers will be preferred, particularly those having a styrene content of between 25 and 45% by weight with respect to the weight of said SEBS. The product marketed by the company SHELL under the designation KRATON® G 1651 will more particularly be preferred.

In general, the thermoplastic elastomer will be used according to the nature of the block copolymer, in an amount of the order of 2 to 20% by weight with respect to the total weight of the composition. Preferably, a thermoplastic elastomer will be used which has an average molar mass of greater than that of the amphiphilic copolymer, preferably of the order of 100,000 daltons. In this case, the latter thermoplastic elastomer will then preferably be used in an amount of the order of 2 to 10% by weight with respect to the total weight of the composition.

If necessary, it will be possible to add anti-oxidising agents to these block copolymers. The term <<anti-oxidising agent>> is understood here as meaning the compounds which are commonly used by the person skilled in the art for ensuring the stability of the compounds used in the thermoplastic elastomer-based formulations against oxygen, heat, ozone and ultraviolet radiations. One or more of these anti-oxidising agents can be used in combination.

Phenolic anti-oxidising agents, such as, for example, the products marketed by the company CIBA-GEIGY under the designations IRGANOX® 1010, IRGANOX® 565, IRGANOX® 1076, and sulphur-containing anti-oxidising agents, such as, for example, zinc dibutyldithiocarbamate, marketed by the company AKZO under the designation PERKACIT® ZDBC, can be cited as appropriate anti-oxidising agents.

In the solid emulsions according to the present invention, the oily phase is a hydrophobic and lipophilic phase which is constituted by a liquid plasticizer. The term "liquid plasticizer" is designated for plasticizers which are usually used by the person skilled in the art for the preparation of compositions which comprise thermoplastic elastomers, in particular of poly(styrene-olefin-styrene) block copolymer type such as, for example, thermofusible adhesives which are sensitive to pressure and which are products which enable their properties of stretching, flexibility, extrudability or implementation to be improved, and reference may be made in this respect to the prior art documents mentioned above.

These liquid plasticizers are compounds which are compatible with the central olefin sequence of the block copolymers used. Plasticizing oils are used very often as liquid plasticizer, and particularly mineral oils which are formed from compounds of paraffinic, naphthenic or aromatic nature, or their mixtures, in variable proportions.

The products marketed by the company SHELL under the designation ONDINA® and RISELLA® can thus be cited as examples of mineral oils for the mixtures based on naphthenic and paraffinic compounds, or under the designation CATENEX® for the mixtures based on naphthenic, aromatic and paraffinic compounds.

Within the context of the present invention, paraffin oils will be preferred, particularly the oil marketed by the company SHELL under the designation ONDINA® 15.

As liquid plasticizer, not a plasticizing oil, but synthetic products based on liquid mixtures of saturated hydrocarbons can also be used, such as, for example, the products marketed by the company TOTAL under the designation GEMSEAL, particularly such as the product GEMSEAL° 60 which is an isoparaffinic mixture originating from a totally hydrogenated petroleum fraction.

Within the context of the preparation of solid emulsions according to the invention, a concentration of liquid plasticizer will preferably be used of the order of 25 to 90% by weight with respect to the total weight of the solid emulsion, preferably 30 to 75% by weight with respect to the total weight of the solid emulsion.

The aqueous phase of the solid emulsions according to the invention is mainly water. It will be possible to use any type of water according to the fields of application envisaged such as, for example, spring water, tap water, demineralised, purified, deionised, or sterilised water.

It will of course be possible to incorporate any adjuvant with this water which is useful for preserving these properties of purity or of sterility with time, or any products which are generally used in the preparation of a classical emulsion which are incorporated in the aqueous phase. Of course, the person skilled in the art will take care so that the introduction or the proportions of these products does not come to alter the properties of cohesion and of elasticity of the solid emulsions obtained.

Similarly, according to the application sought after, it will be possible to introduce very low amounts of water of the order of 1% by weight with respect to the total weight of the emulsion or of large amounts ranging up to 60% or more by weight with respect to the total weight of the solid emulsion.

Within the context of the present invention, solid emulsions are preferred which comprise of the order of 5 to 6560% by weight of water and more particularly 10 to 6050% by weight with respect to the total weight of the solid emulsion.

A solid emulsion which is currently preferred according to the invention comprises:

a. 2 to 10 parts by weight of a thermoplastic elastomer of average molar mass greater than or equal to 100,000 daltons, b. 30 to 7590 parts by weight of liquid plasticizer, c. 2 to 50 parts by weight of water, and d. 0.05 to 5 parts by weight of an amphiphilic ABA type block copolymer comprising two terminal thermoplastic poly(styrene) blocks A and one central elastomeric block B, in which the central block B is a poly(ethylene-butylene) sequence comprising grafted hydrophilic groups, it being possible for said amphiphilic copolymer ABA to be. represented schematically by the following structure:

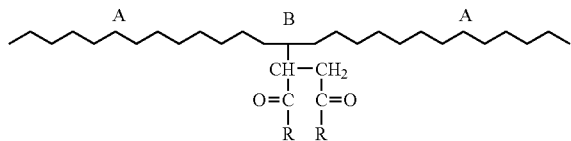

in which R represents a $CH_3-O-(CH_2-CH_2-O)_n$ group of average molar mass equal to 2000, i.e. n=45, and which has an average molar mass measured by gel permeation chromatography of 50,000 daltons.

Just as the classical emulsions and the gels based on block copolymers described above, the solid emulsions according to the invention can be used in multiple fields by virtue of their excellent capacity to be shaped and of their hydrophilic character which can be regulated easily as a function of the use sought after.

The solid emulsions according to the invention are in fact thermofusible products which are manufactured by melting and mixing the constituents at the melting temperature of the thermofusible elastomer which is used according to the technique which is well-known to the person skilled in the art and which is designated under the name of the method "hot melt". By virtue of the rheological properties of the solid emulsions according to the invention, the homogeneous mixture finally obtained can therefore be shaped or combined with other elements, before cooling, in order to prepare a final product.

Thus, final products can be prepared in various geometrical shapes by moulding or extrusion such as, for example, shapable sheets of variable thickness, spaghettis, films, granules, etc . . . . The hot solid emulsion can also be deposited on a support forming element, e.g. by coating.

All these possibilities offer very many advantages and prove to be particularly useful in the preparation of products for medical, dermatological, pharmaceutical or cosmetic purposes. It will be possible for the solid emulsions according to the invention to be incorporated easily into any device intended to be placed in contact with the skin, a wound or the mucous membranes, e.g. a dressing or a bandage for treating or protecting the skin, a wound, burns, a blister, deep, chronic or grave superficial dermo-epidermic lesions ; a patch for the topical or systemic release of actives; a product for cleansing or care of the skin, such as, for example, a scaling or anti-wrinkle product; or even an electrode, etc . . . .

The solid emulsions according to the invention can also be used alone, in cosmetology or dermatology for the preparation of gels or ointments that can be removed in one single piece, or in the field of the treatment of burns, for the preparation of shapable cover sheets, or even in surgery for the preparation of an implantable biocompatible material, e.g. an abdominal wall reinforcement, etc . . . .

Additionally, by virtue of their aptitude to contain water or a hydrophilic active in a medium having a high hydrophobic content and vice versa, various compounds can be incorporated during the formulation of the solid emulsion. These compounds can be adjuvants or actives which are commonly used in the dermatological, cosmetic or pharmacological fields. Antioxidants, preservatives, perfumes, fillers, odour absorbers, colouring materials, UV filters, electrolytes for carrying current, pH regulators, bactericides, magnetisable particles, microcapsules or microspheres can be cited as adjuvants which can thus be incorporated.

The amounts of these various adjuvants are those which are classically used in the field considered and for example 0.01 to 20% by weight with respect to the total weight of the emulsion. One or more actives selected from the following list can be incorporated as active agent: vitamins and their derivatives, glycerine, collagen, salicylic acid, aromatic essential oils, caffeine, anti-free radical actives, hydrating actives, depigmenting actives (such as kojic acid), liporegulating actives, anti-acne actives, anti-ageing actives, softening actives, decongesting actives, anti-wrinkle actives, refreshing actives, keratolitic agents and healing accelerating agents, vascular protecting agents, anti-bacterial agents such as sulfadiazine silver, anti-fungal agents, anti-perspirant agents, deodorant agents, skin conditioning agents, anaesthetising compounds, immunomodulators, nourishing agents, plant extracts such as, for example, green tea, Arnica, hamamelis . . . , trace elements, local anaesthetics, anti-inflammatories, hormones, menthol, retinoids, DHEA, extracts of algae, of fungi, of yeast, of bacteria, hydrolysed, partially hydrolysed or non-hydrolysed proteins. This list is of course non-limiting.

The active(s) can for example be present at a concentration in the range of 0.01 to 20%, preferably 0.1 to 5%, better 0.5 to 3% of the total weight of the emulsion.

These adjuvants or these actives, according to their nature, can be introduced into the hydrophobic and lipophilic phase or into the aqueous phase. Of course, the person skilled in the art will take care to select the eventual additional actives or adjuvants and/or their amount such that the advantageous properties of cohesion, and of elasticity of the solid emulsion according to the invention not be or substantially not be altered by the addition envisaged.

Within the context of the preparation of products for medical, dermatological or cosmetic purposes such as, for example, patches, dressings, electrodes . . . , the solid emulsion which serves as a reservoir of actives or of adjuvants is in general combined with a support.

Given that the solid emulsion is thermofusible, in this case the coating of the emulsion is carried out onto an adequate support of desired grammage, according to the technique which is well-known to the person skilled in the art, designated under the name "hot melt". It will be possible for the final product to be fixed onto the skin, a wound or the mucous membranes with the aid if necessary of an adhesive, e.g. a peripheral adhesive.

The choice of the support is made as a function of the properties which are required (waterproofness, elasticity, etc . . . ) according to the type of product and the application sought after.

It can be presented as a film of variable thickness of 5 to 150 µm or as a non-woven, or a foam having a thickness of 10 to 500 µm. These supports based on synthetic or natural materials are those which are generally used by the person skilled in the art in the field of the applications mentioned above.

Polyethylene foams, polyurethane foams, PVC foams, polypropylene, polyamide, or polyester non-wovens, or complexes made based on a film and on a non-woven, etc. can thus be cited.

Practically, it will be possible for the surface of the solid emulsion which is not linked to the support to be covered with a protective layer or film which can be peeled off before use of the product. It will be possible for the whole thus formed to be itself packaged in a waterproof protection made for example by means of polyethylene-aluminium complexes or in blisters.

The characteristics and applications of the invention will be better understood upon reading the following description of Examples of embodiments. The whole of these elements is of course in no way limiting, but is given solely as an illustration.

For reasons of simplicity, an example of synthesis of a representative amphiphilic copolymer will first of all be given which will be used in all the adhesive compositions given as Examples which follow.

The method of synthesis of this copolymer is described in the Preparation I below.

A reactor equipped with a condenser, equipped with a drier, a sieve linked to the vacuum and to nitrogen if the reaction is carried out under an inert atmosphere, and a Dean-Stark, for removing the water formed by azeotropic distillation, are used in order to carry out the synthesis of this latter copolymer.

Preparation I 150 ml of toluene are introduced under nitrogen in a reactor. 20 g of Kraton G 1901® (maleated SEBS copolymer), marketed by the company SHELL, are added. Heat is given under reflux (about 110° C.) under agitation until total dissolution of the maleated SEBS copolymer. A solution of PEGME of molar mass 2,000, marketed by the company Aldrich under the designation poly(ethyleneglycol)methyl-ether 2000, is prepared apart. 32.32 g of PEGME 2000 are thus dissolved under agitation by heating at its melting temperature in 100 ml of toluene. About 20 drops of sulphuric acid are added to the solution of maleated SEBS copolymer obtained beforehand, still under agitation and under reflux. The solution of PEGME 2000 in toluene prepared beforehand is then added, still under agitation and under reflux. Thus, in this case, there are 4 hydroxyl functions for each anhydride function. The mixture obtained is kept agitated under reflux until the completion of the reaction of esterification, i.e. here about 30 to 40 minutes. The solution is then precipitated in the hot, at about 90 to 100° C., in 1.5 l of a 50/50 water-ethanol mixture. After filtration, the residual solvents are removed from the precipitate obtained by evaporation in the oven under vacuum at 40-50° C. It is necessary to remove the excess PEGME 2000 which has not reacted during the synthesis, in order to purify the amphiphilic polymer obtained. For this, the amphiphilic polymer is re-dissolved in the hot at about 90-100° C., with agitation, in 100 to 150 ml of toluene, and the solution obtained is again precipitated in 1.5 litres of a 50/50 water/ethanol mixture. After filtration, the recovered precipitate is dried under vacuum at 40-50° C. This purification step is repeated (re-dissolution-precipitation and drying under vacuum) until the PEGME 2000 is totally removed. An amphiphilic copolymer is thus obtained in which $R_1$ and $R_2$ represent a $CH_3$—O—$(CH_2—CH_2—O—)_n$ group in which n=45 which has an average molar mass of the order of 50,000 daltons, measured by gel permeation chromatography, with tetrahydrofuran as solvent, at a rate of 1 ml per minute, on a column marketed by the company WATERS under the designation STYRAGEL HR4, and with a refractive index detector.

EXAMPLES OF SOLID EMULSIONS ACCORDING TO THE INVENTION

Several solid emulsions according to the invention have thus been prepared according to the following preparation method:

The mixture of the various constituents is made in a closed reactor, heated at a temperature which ranges between 100 and 130° C., according to the nature of the thermoplastic elastomer, so as to melt this latter mixture.

The agitation is made by virtue of a mixer equipped with a deflocculating helix at a speed of about 500 rpm.

Firstly, the amphiphilic copolymer, the water, the liquid plasticizer and all the other compounds, actives or adjuvants, which are not susceptible to being degraded at this temperature, except the thermoplastic elastomer, are introduced into the reactor heated between about 100 and 130° C. The mixture thus formed is then agitated continuously until a homogeneous mixture is obtained.

Secondly, the thermoplastic elastomer is incorporated into this mixture and agitation is continued keeping between 100 to 130° C., until a homogeneous mixture is obtained. If necessary, the thermoplastic elastomer can be mixed and melted with a small part of the liquid plasticizer before incorporation, in order to facilitate its homogenisation with the preceding mixture.

If necessary, the temperature is allowed to cool to less than 100° C. and any compound which is susceptible to being degraded at a higher temperature, such as, for example, liposoluble or hydrosoluble adjuvants and actives, such as a dry extract of Arnica in Example 1, is then incorporated, and agitation is done until a homogeneous mixture is obtained.

The solid emulsion is then ready to be used e.g. moulded, extruded, or even incorporated in a product by coating.

The constituents used for the preparation of the solid emulsions described below are the following:

| | |
|---|---|
| PREPARATION I | amphiphilic copolymer |
| KRATON D 1161 ® | SIS marketed by the company SHELL |
| ONDINA 15 ® | mineral oil marketed by the company SHELL |
| GEMSEAL ® 60 | liquid mixture of saturated hydrocarbons marketed by the ecompany TOTAL |
| WATER | |
| EXTRACT OF ARNICA | hydrophilic active |

The amounts of the various constituents of these solid emulsions, expressed as a percentage by weight with respect to the total weight of the solid emulsion, are grouped together in Table I.

TABLE I

| | EX. 1 | EX. 2 | EX. 3 | EX. 4 | EX. 5 | EX. 6 |
|---|---|---|---|---|---|---|
| PREPARATION I | 0.1 | 2 | 0.5 | 1 | 1 | 0.25 |
| KRATON D 1161 ® | 10 | 2 | 9 | 5 | 10 | 10 |
| ONDINA 15 ® | | 44 | 66 | | | |
| GEMSEAL ® 60 | 62.1 | | | 47 | 66 | 70 |
| WATER | 19.8 | 52 | 25 | 47 | 23 | 25 |
| EXTRACT OF ARNICA | 8 | | | | | |

The Examples of Table I illustrate the advantages of the invention. It is noted that the incorporation of very low amounts of amphiphilic copolymers of the order of 0.1 to 0.5% by weight with respect to the total weight of the solid emulsion, into the Examples 1, 3 and 6, enable up to 20 to 25% of water to be incorporated with a hydrophobic gel based on KRATON®D and liquid plasticizer.

Similarly, 8% by weight of a hydrophilic active principle, an extract of Arnica, was incorporated into the solid emulsion of Example 1.

If necessary, this solid emulsion can be coated in the hot onto a support with a peripheral adhesive and a patch of Arnica is then obtained for example which provides freshness and activity of the Arnica, for treating knocks and bumps. Optionally, a support may not be used and a film or a sheet containing Arnica can be made directly which can be applied on the skin with the aid of a band.

Finally, in Examples 2 and 4, it is noted that solid emulsions based on KRATON®D 1161, containing up to 50% of water, are obtained.

Furthermore, the rheological properties of a solid emulsion according to the invention were compared to those of a classical emulsion by testing their capacities of deformation under constraint.

Thus, a solid emulsion according to the invention was tested, that of Example 5, and a classical emulsion constituted by the product marketed by the company URGO under the designation URGO® brulures ("burns").

The test conditions are the following

Material and equipment

A BOHLIN rheometer (type CS) was used having imposed constraint. The test is carried out at the temperature of 25° C.

The principle of the test of relaxation of constraint is the following

A constraint which is sufficient to deform the sample is applied for 60 seconds.

This constraint is then removed and the resulting deformation γ, expressed as a percentage, of the sample, is measured for 120 seconds.

The apparatus provides curves directly which illustrate the properties of deformation of the sample.

In the present case, the two products have very different properties and the same constraint cannot therefore be applied.

In fact, with the apparatus used under a constraint of 50 Pascals, the deformation of the solid emulsion is insufficient to be measured, while under a constraint of 100 pascals, in the case of a classical emulsion, the measurement cannot be made since a part of the emulsion is projected, under the effect of the rotation, outside the plates.

The implementation conditions of the test with the BOHLIN rheometer on each product have therefore been adapted in order to take into account these elements and to nevertheless have comparable results.

Burn Emulsion:

The sample to be analysed (about 1 gram) is placed between a stationary lower plane and an upper cone (diameter 40 mm, angle 40 degrees).

Solid Emulsion of Example 5:

The sample to be analysed (about 1 gram) is placed between two parallel plates (diameter 20 mm, distance between the plates 1 mm). Good care is taken that the sample deposited does not extend past the plates.

The constraint applied onto the URGO® burns emulsion is therefore of 50 Pascals and that applied onto the solid emulsion of Example 5 is of 100 Pascals.

This difference in value of the constraint applied already illustrates in itself the advantages of the solid emulsions according to the invention with respect to the classical emulsions in terms of cohesion and of elasticity.

Figure 2:
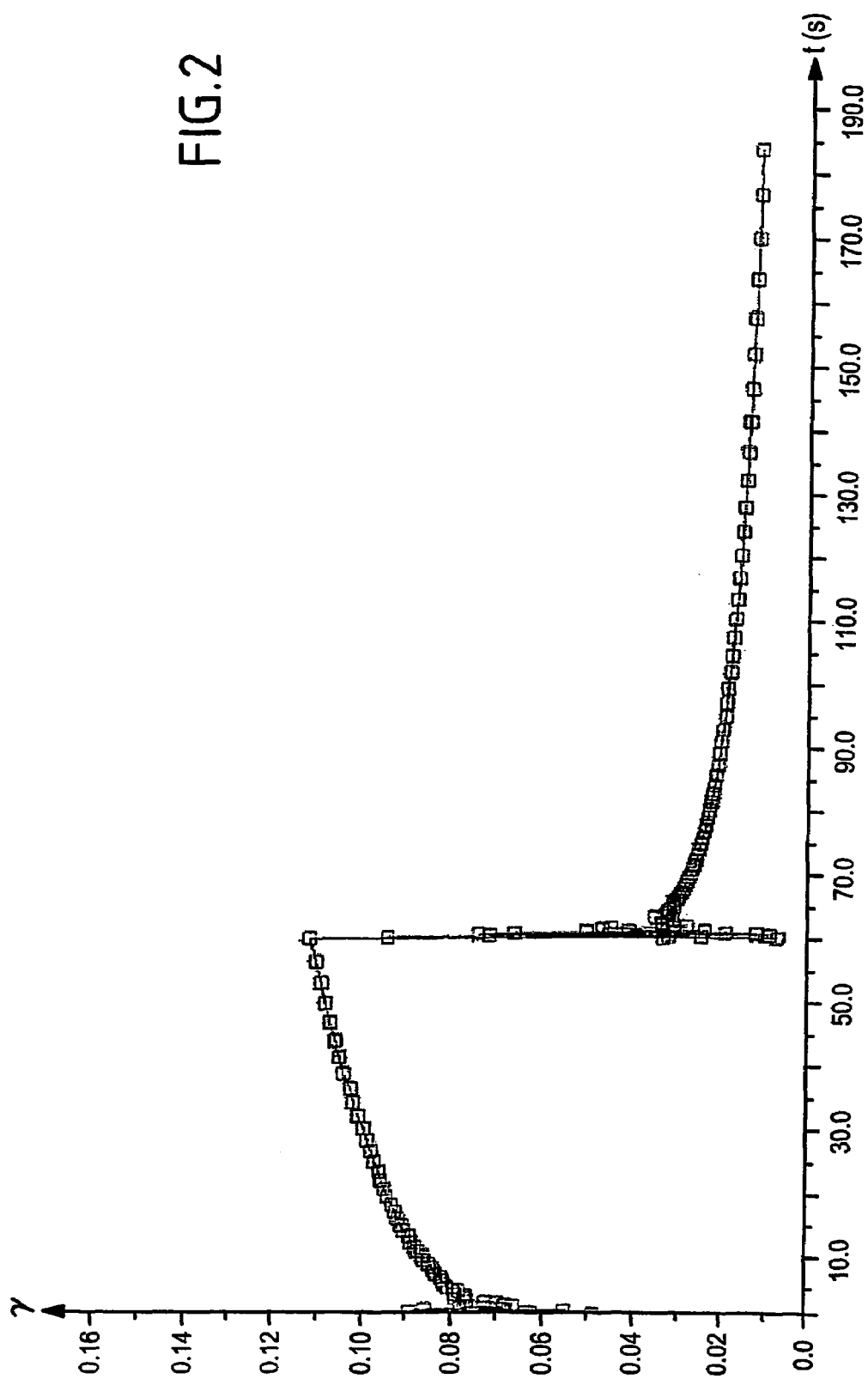

The results obtained are illustrated on FIGS. 1 and 2 which respectively relate to the burn emulsion for FIG. 1 and the solid emulsion of Example 5 for FIG. 2.

On these two Figures, the time, expressed in seconds, is on the abscissa, and the resulting deformation, $\gamma \times 10^3$, expressed as a percentage, in FIG. 1, and γ, expressed as a percentage, in FIG. 2, on the ordinate.

The comparison of the two curves very clearly demonstrates the differences in terms of rheological, elasticity and cohesion properties, between a classical emulsion and a solid emulsion according to the invention.

On FIG. 1, it is seen that the classical emulsion has a purely viscous character. Under a given constraint, the deformation increases linearly with time. It varies in this Example of the order of 26%.

Once the constraint is removed, there is no return to the initial state. A straight horizontal line is obtained, which characterises a total absence of elastic, and therefore cohesive, character.

On the contrary, it is seen on FIG. 2 that the solid emulsion according to the invention presents a visco-elastic behaviour.

Under a given constraint, (double that exerted on the classical emulsion), the deformation is much lower of the order of 0.10%. Furthermore, in contrast to the classical emulsion, after the removal of the constraint, the solid emulsion tends to regain its initial state (a straight line is not observed) and the resulting deformation γ tends towards 0.

Therefore, the product is elastic and therefore cohesive.

It is these rheological properties which enable solid emulsions to be obtained the hardness of which can be regulated by thus providing a wide range of elastic and cohesive products ranging from gel to solid, with the advantages mentioned above.

The invention claimed is:

1. A solid emulsion, which comprises:
   a thermoplastic elastomer, which is selected from the group consisting of poly(styrene-olefin-styrene) block copolymers, poly(styrene-olefin) block copolymers and their mixtures,
   an oily phase, which is constituted of a liquid plasticizer,
   an aqueous phase, and
   an amphiphilic ABA type block copolymer comprising two terminal thermoplastic poly(styrene) blocks A and one central elastomeric block B, in which the central block B is a poly(ethylene-butylene) sequence comprising grafted hydrophilic groups, it being possible for said amphiphilic copolymer ABA to be represented schematically by the following structure:

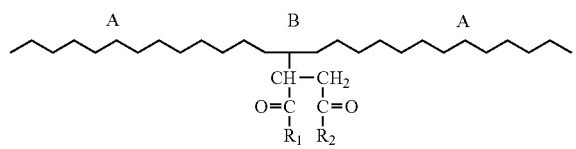

in which $R_1$ and $R_2$, which are identical or different, represent a hydrophilic group of average molar mass of less than 10,000, selected from the group consisting of:

$$CH_3-O-(CH_2-CH_2-O)_n; \quad HO-(CH_2-CH_2-O)_n; \text{ and}$$

$$HO-(CH_2-CH_2-O)_a-(CH-CH_2-O)_b-(CH_2-CH_2-O-)_a;$$
$$\quad\quad\quad\quad\quad\quad\quad\quad\quad\quad\quad\quad |$$
$$\quad\quad\quad\quad\quad\quad\quad\quad\quad\quad\quad\quad CH_3$$

in which n, a and b represent an integer.

2. The solid emulsion according to claim 1, wherein the amphiphilic copolymer is an amphiphilic ABA type block copolymer comprising two terminal thermoplastic poly(styrene) blocks A and one central elastomeric block B, in which the central block B is a poly(ethylene-butylene) sequence comprising grafted hydrophilic groups, it being possible for said amphiphilic copolymer ABA to be represented schematically by the following structure:

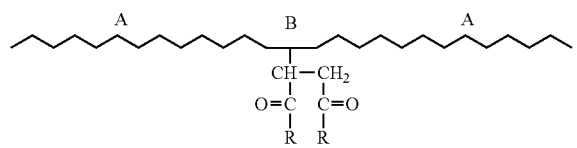

in which R represents a $CH_3$—O—$(CH_2$—$CH_2$—$O)_n$ group of average molar mass equal to 2000, i.e. n=45.

3. The solid emulsion according to claim 2, wherein the amphiphilic copolymer has an average molar mass measured by gel permeation chromatography of the order of 50,000 daltons.

4. The solid emulsion according to claim 1 which comprises 0.05 to 20%, by weight, of amphiphilic copolymer with respect to the total weight of the solid emulsion.

5. The solid emulsion according to claim 1 wherein the liquid plasticizer constituting the oily phase is a plasticizing oil or a liquid mixture of saturated hydrocarbons, which is compatible with the central olefin sequence of the thermoplastic elastomer.

6. The solid emulsion according to claim 5, comprises 25 to 90% by weight, of liquid plasticizer with respect to the total weight of the solid emulsion.

7. The solid emulsion according to claim 1 wherein the thermoplastic elastomer is a mixture of poly(styrene-olefin-styrene)copolymer and of poly(styrene-olefin)copolymer.

8. The solid emulsion according to claim 1 wherein the olefin sequence of the thermoplastic elastomer cited above is selected from the group consisting of: isoprene, butadiene, ethylene-butylene and ethylene-propylene.

9. The solid emulsion according to claim 1 wherein the thermoplastic elastomer is present at a concentration of 2 to 20% by weight with respect to the total weight of the solid emulsion.

10. The solid emulsion according to claim 1 wherein the thermoplastic elastomer has an average molar mass greater than that of the amphiphilic copolymer.

11. The solid emulsion according to claim 1 which comprises 5 to 60% by weight of water, with respect to the total weight of the solid emulsion.

12. A solid emulsion which comprises:
a. 2 to 10 parts by weight of a thermoplastic elastomer of average molar mass greater than or equal to 100,000 daltons,
b. 30 to 75 parts by weight of liquid plasticizer,
c. 2 to 50 parts by weight of water, and
d. 0.05 to 5 parts by weight of an amphiphilic ABA type block copolymer comprising two terminal thermoplastic poly(styrene) blocks A and one central elastomeric block B, in which the central block B is a poly(ethylene-butylene) sequence comprising grafted hydrophilic groups, it being possible for said amphiphilic copolymer ABA to be represented schematically by the following structure:

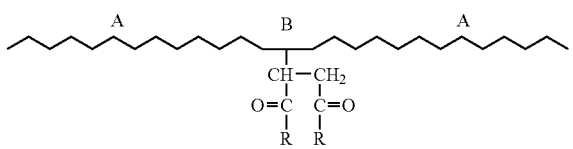

in which R represents a $CH_3$—O—$(CH_2$—$CH_2$—$O)_n$ group of average molar mass equal to 2000, i.e. n=45, and which has an average molar mass measured by gel permeation chromatography of 50,000 daltons.

13. A product selected from the group consisting of medical, dermatological, cosmetological, pharmaceutical and surgical purposes products which comprises a solid emulsion according to claim 1.

14. A product as claimed in claim 13 which is applied on the skin, a wound or the mucous membranes.

15. A product as claimed in claim 13 which is selected from the group consisting of a dressing for treating or protecting a wound, a blister, burns, or superficial dermo-epidermic lesions, a patch for delivering actives via the topical or systemic route, a product for the care, the cleansing or the protection of the skin or of the mucous membranes, an electrode, or a sheet and a shapable film.

16. The solid emulsion according to claim 5 wherein the liquid plasticizer constituting the oily phase is a liquid paraffin.

17. The solid emulsion according to claim 1 wherein the thermoplastic elastomer has an average molar mass greater than that of the amphiphilic copolymer, and is present at a concentration of 2 to 10% by weight with respect to the total weight of the solid emulsion.

* * * * *